United States Patent
Brandt et al.

(10) Patent No.: US 11,491,093 B2
(45) Date of Patent: Nov. 8, 2022

(54) COMPOSITIONS COMPRISING SORBITAN CARBOXYLIC ESTERS AND GLYCEROL CARBOXYLIC ESTERS

(71) Applicant: Evonik Operations GmbH, Essen (DE)

(72) Inventors: Kathrin Daniela Brandt, Düsseldorf (DE); Dominik Schuch, Düsseldorf (DE); Beata Bednorz, Essen (DE)

(73) Assignee: Evonik Operations GmbH, Essen (DE)

( * ) Notice: Subject to any disclaimer, the term of this patent is extended or adjusted under 35 U.S.C. 154(b) by 315 days.

(21) Appl. No.: 16/857,523

(22) Filed: Apr. 24, 2020

(65) Prior Publication Data
US 2020/0375862 A1    Dec. 3, 2020

(30) Foreign Application Priority Data

May 28, 2019  (EP) .................... 19176865

(51) Int. Cl.
*A61K 8/37*    (2006.01)
*A61K 8/49*    (2006.01)

(52) U.S. Cl.
CPC ............ *A61K 8/375* (2013.01); *A61K 8/4973* (2013.01)

(58) Field of Classification Search
CPC ................. A61K 8/375; A61K 8/4973
See application file for complete search history.

(56) References Cited

U.S. PATENT DOCUMENTS

| | | |
|---|---|---|
| 8,466,248 B2 | 6/2013 | Meyer et al. |
| 8,642,525 B2 | 2/2014 | Herrwerth et al. |
| 8,993,792 B2 | 3/2015 | Hartung et al. |
| 9,409,853 B2 | 8/2016 | Schuch et al. |
| 9,616,007 B2 | 4/2017 | Herrwerth et al. |
| 9,890,107 B2 | 2/2018 | Schuch et al. |
| 10,370,493 B2 | 8/2019 | Brandt et al. |
| 10,544,384 B2 | 1/2020 | Scheuermann et al. |
| 10,618,867 B2 | 4/2020 | Liebig et al. |
| 10,676,495 B2 | 6/2020 | Lu et al. |
| 2012/0015893 A1* | 1/2012 | Herrwerth ............... A61Q 5/12 514/23 |
| 2013/0171087 A1* | 7/2013 | Herrwerth ............... A61Q 5/12 514/552 |
| 2018/0344602 A1 | 12/2018 | Schuch et al. |
| 2019/0040095 A1 | 2/2019 | Lu et al. |
| 2019/0269158 A1 | 9/2019 | Schilling et al. |
| 2019/0307657 A1 | 10/2019 | Wenk et al. |

FOREIGN PATENT DOCUMENTS

| | | |
|---|---|---|
| DE | 10 2008 001 788 A1 | 11/2009 |
| EP | 2410979 A2 | 2/2012 |
| WO | 2009/135007 A1 | 11/2009 |
| WO | 2010/108738 A2 | 9/2010 |
| WO | 2012/062519 A1 | 5/2012 |

OTHER PUBLICATIONS

European Search Report dated Dec. 6, 2019 in EP 19176865.4 (5 pages).

* cited by examiner

*Primary Examiner* — Jeffrey S Lundgren
*Assistant Examiner* — Ibrahim D Bori
(74) *Attorney, Agent, or Firm* — Taylor English Duma LLP; Philip P. McCann

(57) ABSTRACT

The invention relates to compositions comprising certain sorbitan carboxylic esters and glycerol carboxylic esters in particular amounts.

19 Claims, No Drawings

COMPOSITIONS COMPRISING SORBITAN CARBOXYLIC ESTERS AND GLYCEROL CARBOXYLIC ESTERS

CROSS REFERENCE TO RELATED APPLICATIONS

This application is a 35 U.S.C. § 119 patent application which claims the benefit of European Application No. 19176865.4 filed May 28, 2019, which is incorporated herein by reference in its entirety.

FIELD

The invention relates to compositions comprising certain sorbitan carboxylic esters and glycerol carboxylic esters in particular amounts.

BACKGROUND

EP2410979 discloses the use of sorbitan carboxylic esters, in which the carboxylic acid part is derived from a carboxylic acid comprising 6 to 10 carbon atoms and which have a hydroxyl number (OH number) of greater than 350, as viscosity regulators, care active ingredients, foam boosters or solubilizers in cleaning or caring formulations.

The object of the invention was to provide compositions which have very good thickening performance.

SUMMARY

It has been found that, surprisingly, the compositions comprising certain sorbitan carboxylic esters and glycerol carboxylic esters described below are able to achieve the object addressed by the invention.

The present invention therefore relates to compositions comprising sorbitan carboxylic esters and glycerol carboxylic esters and also water as described herein.

DETAILED DESCRIPTION

The present invention further relates to a process for preparing formulations with particular viscosities using the compositions according to the invention.

The present invention still further relates to the use of the compositions according to the invention for increasing the viscosity of a cosmetic or pharmaceutical formulation.

One advantage of the compositions according to the invention is that they have better processability than the individual components.

The compositions according to the invention can be more rapidly incorporated homogeneously into cosmetic formulations under the same boundary conditions than the individual components. A further advantage of the compositions according to the invention is that they exhibit better thickening performance in cosmetic formulations than the individual components.

A further advantage of the compositions according to the invention is that they have better skin-care and sensory properties than the individual components.

The present invention therefore relates to a composition comprising

A) at least one sorbitan carboxylic ester of at least one carboxylic acid selected from carboxylic acids having 6 to 12, preferably 8 to 10, carbon atoms, wherein all sorbitan carboxylic esters present in component A together have on average a degree of esterification of 0.7 to 2.1, preferably 0.9 to 1.9, particularly preferably 1.3 to 1.7, carboxylic ester radicals per sorbitan carboxylic ester, B) at least one glycerol carboxylic ester of at least one carboxylic acid selected from carboxylic acids having 6 to 22, preferably 12 to 18, carbon atoms, wherein all glycerol carboxylic esters present in component B together have on average a degree of esterification of 0.7 to 1.5, preferably 1.0 to 1.4, carboxylic acid radicals per glycerol carboxylic ester, and C) water, characterized in that components A) and B) in sum total are present to an extent of at least 50% by weight, preferably to an extent of at least 65% by weight, particularly preferably to an extent of at least 75% by weight, especially to an extent of at least 85% by weight, based on the total composition.

Unless stated otherwise, all percentages (%) given are percentages by mass.

Sorbitan esters have long been known as good and mild emulsifiers.

Sorbitol is the reduced polyol form of glucose, belongs to the sugar alcohols and is also known under the names sorbitol or glucitol.

Sorbitol can self-condense with elimination of water thus forming so-called sorbitan. Sorbitan is generally understood to mean a product mixture of the self-condensation products of sorbitol; these are essentially five- and six-membered, mono- and bicyclic, hydroxy-functional ethers of polyol character, as represented by way of example by the following formulae:

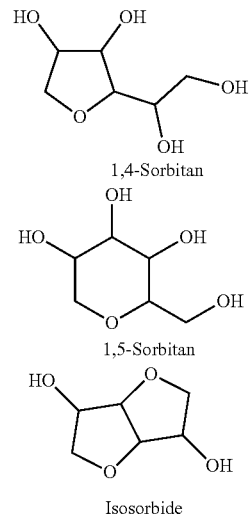

Further condensation products are generally present in this mixture to a lesser extent and also sorbitol.

Sorbitan carboxylic esters are the carboxylic esters of sorbitan and therefore the acylation products of this polyol mixture described above, where the polyol mixture has generally been acylated with 1 to 3 mol of carboxylic acid per 1 mol of polyol; however, substoichiometric acylations are also conceivable in which the polyol mixture is acylated with less than 1 mol of carboxylic acid per 1 mol of polyol. The average degrees of esterification specified for the sorbitan carboxylic esters in the context of the invention refer to the molar ratio of carboxylic acid to the sorbitol used for the self-condensation.

An overview summary of sorbitan esters is found, for example, in Treon, Soap Perfumary Cosmetics, January 1965, p. 47.

The glycerol carboxylic esters present in component B may have on average a degree of esterification of less than 1, which corresponds to a substoichiometric acylation product of glycerol with carboxylic acid. Such glycerol carboxylic esters therefore comprise glycerol.

It is preferable in accordance with the invention if component A) has a saponification number of 100 to 300, preferably 130 to 280, particularly preferably 160 to 260 mg KOH/g.

It is preferable in accordance with the invention if component B) has a saponification number of 100 to 300, preferably 115 to 265, particularly preferably 130 to 230 mg KOH/g.

Suitable methods for determining the saponification number of components A) and B) are disclosed in DGF C-V 3, DIN EN ISO 3681 and Ph. Eur. 2.5.6; these methods developed originally for fats can be applied without any problem to the components of the invention.

A preferred composition according to the invention comprises
A) at least one sorbitan carboxylic ester of at least one carboxylic acid selected from carboxylic acids having 8 to 10 carbon atoms, wherein all sorbitan carboxylic esters present in component A together have on average a degree of esterification of 1.3 to 1.7 carboxylic acid radicals per sorbitan carboxylic ester,
B) at least one glycerol carboxylic ester of at least one carboxylic acid selected from carboxylic acids having 12 to 18 carbon atoms, wherein all glycerol carboxylic esters present in component B together have on average a degree of esterification of 0.7 to 1.5 carboxylic acid radicals per glycerol carboxylic ester, and
C) water,
and is characterized in that components A) and B) in sum total are present to an extent of at least 65% by weight, preferably to an extent of at least 75% by weight, particularly preferably to an extent of at least 85% by weight, based on the total composition.

A preferred composition according to the invention is characterized in that said composition comprises
20 to 75, preferably 30 to 65, particularly preferably 40 to 55, parts by weight of component A),
20 to 75, preferably 30 to 65, particularly preferably 40 to 55, parts by weight of component B), and
0.01 to 50, preferably 0.1 to 30, particularly preferably 1 to 10, parts by weight of water.

It is preferred in accordance with the invention that in the composition according to the invention component B) comprises at least 70, preferably at least 80% by weight of glycerol monocarboxylic ester, wherein the percentages by weight refer to all glycerol carboxylic esters of component B).

A preferred composition according to the invention is characterized in that the carboxylic acids of the carboxylic esters of components A) and B) are selected from fatty acids.

It is preferred in accordance with the invention that in the composition according to the invention the carboxylic acid of the sorbitan carboxylic ester of component A) is selected from caprylic acid and capric acid. A particularly preferred composition according to the invention is characterized in that the carboxylic acid of the sorbitan carboxylic ester of component A) is a mixture of caprylic acid and capric acid, preferably with a ratio by weight of caprylic acid to capric acid in a range from 6:1 to 2:1, preferably 4:1 to 3:1.

It is preferred in accordance with the invention that in the composition according to the invention the carboxylic acid of the glycerol carboxylic ester of component B) is selected from lauric acid and oleic acid, preferably oleic acid.

A preferred composition according to the invention is characterized in that said composition has a viscosity of 50 to 5000, preferably 100 to 3000 mPa s, measured at 25° C. with a Brookfield viscometer using spindle 62 and at 30 rpm.

The compositions according to the invention are concentrates with which formulations can be prepared in an advantageous manner, in which the active ingredient concentration is in the customary application range.

Therefore, the present invention further relates to a process for preparing a cosmetic or pharmaceutical formulation, in particular having a viscosity of 500 to 15 000 mPa s, preferably 1000 to 10 000 mPa s, measured at 25° C. with a Brookfield viscometer using spindle 62 and at 30 rpm, comprising the process steps of
I) providing a composition according to the invention,
II) mixing the composition according to the invention with further cosmetic or pharmaceutical formulation constituents to obtain a formulation having a content of component A) and component B) in sum total in a range of 0.1% by weight to 5.0% by weight, preferably 0.2% by weight to 2.5% by weight, wherein the percentages by weight refer to the total formulation.

In the process according to the invention for preparing a cosmetic or pharmaceutical formulation, suitable formulation constituents used in process step II) are, for example:
emollients,
emulsifiers,
thickeners/viscosity regulators/stabilizers,
UV light protection filters,
antioxidants,
hydrotropes (or polyols),
solids and fillers,
film formers,
pearlescence additives,
deodorant and antiperspirant active ingredients,
insect repellents,
self-tanning agents,
preservatives,
conditioning agents,
perfumes,
dyes,
odor absorbers,
cosmetic active ingredients,
care additives,
superfatting agents,
solvents.

Substances which can be used as exemplary representatives of the individual groups are known to those skilled in the art and can be found for example in German application DE 102008001788.4. This patent application is hereby incorporated as reference and thus forms part of the disclosure.

As regards further optional components and the amounts used of these components, reference is made expressly to the relevant handbooks known to those skilled in the art, for example K. Schrader, "Grundlagen and Rezepturen der Kosmetika [Cosmetics—fundamentals and formulations]", 2nd edition, pages 329 to 341, Hüthig Buch Verlag Heidelberg. The amounts of the particular additives are determined by the intended use.

Typical boundary formulations for the respective applications are known prior art and are contained for example in the brochures of the manufacturers of the particular base and active ingredients. These existing formulations can generally be adopted unchanged. However, if required, for adjustment and optimization, the desired modifications can be undertaken by simple tests without complication.

In the process according to the invention for preparing a cosmetic or pharmaceutical formulation, at least one surfactant in particular is included as formulation constituent used in process step II). The carboxylic esters of the composition according to the invention may have surfactant properties; in the context of the present invention these carboxylic esters are not counted as surfactants.

Surfactants included may be, for example, anionic, non-ionic or amphoteric surfactants.

Typical examples of anionic surfactants are fatty alcohol sulfates, fatty alcohol polyglycol ether sulfates, monoglyceride sulfates, mono- and/or dialkyl sulfosuccinates, fatty acid isethionates, fatty acid sarcosinates, fatty acid taurates, fatty acid glutamates, fatty acid glycinates, alkyl ether carboxylates.

Non-ionic surfactants are, for example, alkyl oligoglucosides, fatty acid glucamides, rhamnolipids, sophorolipids and/or protein fatty acid condensates, the latter for example based on wheat proteins.

Amphoteric surfactants are, for example, alkylamidoalkyl hydroxysultaines, alkylamidoalkyl betaines, alkyl betaines, amphoacetates and amphopropionates, the terminal acyl or alkyl radicals of which typically comprise 8 to 18 carbon atoms.

Surfactants particularly included in accordance with the invention are fatty alcohol sulfates, fatty alcohol polyglycol ether sulfates, mono- and/or dialkyl sulfosuccinates, amphoacetates, amphopropionates, alkyl betaines, cocamidopropyl betaines, alkyl oligoglucosides and fatty acid glutamates.

Surfactants particularly preferably included in accordance with the invention are the polyether-free surfactants mono- and/or dialkyl sulfosuccinates, amphoacetates, amphopropionates, betaines, especially cocamidopropyl betaines, alkyl oligoglucosides and fatty acid glutamates. In accordance with the invention, the preferred amount of surfactant included is used such that the resulting formulation comprises at least 2% by weight, preferably at least 4% by weight and particularly preferably at least 6% by weight total surfactant, based on the total formulation.

A preferred process according to the invention is characterized in that process step II) is carried out in a temperature range of 15° C. to 90° C., preferably 18° C. to 60° C.

It is preferable in accordance with the invention that in process step II) in the process according to the invention a water content is set in a range of 50% by weight to 95% by weight, preferably 80% by weight to 93% by weight, wherein the percentages by weight refer to the total formulation.

A preferred process according to the invention is characterized in that it comprises in process step III) the adjustment of the pH to a range of 4.0 to 8.0, preferably 4.5 to 6.5. The "pH" in connection with the present invention is defined as the value which is measured for the relevant composition at 25° C. after stirring for five minutes using a pH electrode calibrated in accordance with ISO 4319 (1977).

The present invention further relates to the use of a composition according to the invention for increasing the viscosity of a cosmetic or pharmaceutical, preferably surfactant, formulation. Since the carboxylic esters of the composition used according to the invention may have surfactant properties, the term "surfactant formulation" in the context of the present invention is understood to mean a formulation which, in addition to the aforementioned carboxylic esters, comprises at least one further surfactant.

It is apparent that in preferred processes in accordance with the invention in process step I) above, the compositions according to the invention identified as preferred are used.

The same applies to preferred uses according to the invention.

The examples adduced hereinafter illustrate the present invention by way of example, without any intention of restricting the invention, the scope of application of which is apparent from the entirety of the description and the claims, to the embodiments specified in the examples.

EXAMPLES

Example 1: Preparation of a Composition According to the Invention 47.5 g of sorbitan sesquicaprylate and 47.5 g of glyceryl monooleate and 5 g of water were stirred at 60° C. for 30 min and then cooled to 22° C.

Example 2: Incorporation in a Cosmetic Formulation

The formulation constituents in the following compositions are named in the form of the commonly acknowledged INCI nomenclature using the English terms. All concentrations in the application examples are specified in % by weight.

A surfactant formulation consisting of 5.6% Sodium Cocoamphoacetate, 4.4% Lauryl Glucoside, 1.2% Coco-Glucoside and 3.6% Sod./Disod. Cocoyl Glutamate was prepared in water. The pH was adjusted to 5.5 with citric acid. The time required to incorporate 1.0% thickener clearly and homogeneously into this formulation at 22° C. and 30 rpm (anchor stirrer) was determined and is presented in the following table:

TABLE 1

Incorporation time of 1.0% thickener in the example formulation (22° C., anchor stirrer, 30 rpm)

| | Incorporation time [min] |
|---|---|
| Example 1 (inventive**) | 2 |
| Sorbitan sesquicaprylate (non-inventive*) | 5 |
| Glyceryl monooleate (non-inventive*) | no clear homogeneous formulation after 100 min |

The results of table 1 show that less time is required for the clear and homogeneous incorporation of inventive example 1 than for the non-inventive thickeners.

Example 2b: Incorporation in a Cosmetic Formulation

A surfactant formulation consisting of 4.8% sodium cocoamphoacetate, 4.8% cocamidopropyl betaine and 3.6% disodium lauryl sulfosuccinate was prepared in water. The pH was adjusted to 5.5.with citric acid. The time required to incorporate 1.8% thickener clearly and homogeneously into this formulation at 22° C. and 250 rpm (anchor stirrer) was determined and is presented in the following table.

TABLE 1b

Incorporation time of 1.8% thickener in the example formulation
(22° C., anchor stirrer, 250 rpm)

| | Incorporation time [min] |
|---|---|
| Example 1 (inventive**) | 5 |
| Sorbitan sesquicaprylate (non-inventive*) | 6 |
| Glyceryl monooleate (non-inventive*) | no clear homogeneous formulation after 200 min |

The results from table 1b show that less time is required for the clear and homogeneous incorporation of inventive example 1 than for the non-inventive thickeners Example 3: Thickening Performance in a Cosmetic Formulation The thickening effect of inventive example 1 was evaluated in comparison with non-inventive thickeners. For this purpose, a cosmetic formulation consisting of 6.8% Cocamidopropyl Betaine, 5.9% Lauryl Glucoside, 2.8% Coco-Glucoside and 1.5% Sucrose Cocoate was prepared in water. The pH of this formulation was adjusted to 5.5 with citric acid. In each case, 0.5% thickener was incorporated into these formulations and the viscosities measured with the aid of a Brookfield viscometer (spindle 62, 30 rpm) at 22° C. The results of the viscosity measurements are shown in table 2:

TABLE 2

Viscosity of the example formulation with 0.5% thickener

| | Viscosity [mPa s] |
|---|---|
| Example 1 (inventive**) | 2800 |
| Sorbitan sesquicaprylate (non-inventive*) | 2170 |
| Glyceryl monooleate (non-inventive*) | 600 |

The results of table 2 show that higher viscosity formulations are obtained with inventive example 1 than with the non-inventive examples.

Example 4: Skin Care Performance

The improved skin care performance of inventive example 1 was evaluated in comparison with non-inventive examples with the aid of a sensory handwashing test.

For this purpose, a group consisting of 4 trained test persons washed their hands in a defined manner and evaluated the skin softness after washing by means of a grading scale from 1 (very poor) to 5 (very good). The inventive example 1 and the non-inventive examples were each tested in a standardized surfactant formulation consisting of 9% active Sodium Laureth Sulfate and 3% active Cocamidopropyl Betaine (see table 3).

TABLE 3

Test formulations for the handwashing test, pH 5.5,
figures in % active substance

| Formulation examples | I ** | II * | III * |
|---|---|---|---|
| Texapon ® NSO-IS, BASF Cognis, 28%, (INCI: Sodium Laureth Sulfate) | 9.0% | 9.0% | 9.0% |
| TEGO ® Betain F 50, Evonik Industries AG, 38% strength (INCI: Cocamidopropyl Betaine) | 3.0% | 3.0% | 3.0% |

TABLE 3-continued

Test formulations for the handwashing test, pH 5.5,
figures in % active substance

| Formulation examples | I ** | II * | III * |
|---|---|---|---|
| Sodium Chloride | 0.7% | 0.7% | 0.7% |
| Citric acid | q.s. | q.s. | q.s. |
| Water, demineralized | to 100 | to 100 | to 100 |
| Example 1 (inventive**) | 1.1% | | |
| Sorbitan sesquicaprylate (non-inventive*) | | 1.1% | |
| Glyceryl monooleate (non-inventive*) | | | 1.1% |

The sensory test results are summarized in table 4.

TABLE 4

Results of the handwashing test, average values across all test persons

| | Formulation I** | Formulation II* | Formulation III* |
|---|---|---|---|
| Skin softness | 2.50 | 2.25 | 2.25 |
| Skin softness after 3 min | 3.50 | 3.25 | 3.13 |

It is apparent, based on the test results in table 4, that formulation I using inventive example 1 results in an increase in skin softness and thus in an overall better skin feel.

The invention claimed is:

1. A composition comprising
   A) at least one sorbitan carboxylic ester of at least one carboxylic acid selected from carboxylic acids having from 6 to 12, carbon atoms, wherein all sorbitan carboxylic esters present in A) together have on average a degree of esterification of from 0.7 to 2.1, carboxylic acid radicals per sorbitan carboxylic ester,
   B) at least one glycerol carboxylic ester of at least one carboxylic acid selected from carboxylic acids having from 6 to 22, carbon atoms, wherein all glycerol carboxylic esters present in component B together have on average a degree of esterification of from 0.7 to 1.5 carboxylic acid radicals per glycerol carboxylic ester, and
   C) water,
   wherein components A) and B) in sum total are present to an extent of at least 50% by weight of the composition.

2. The composition according to claim 1, wherein A) has a saponification number of from 100 to 300 mg KOH/g.

3. The composition according to claim 1, wherein B) has a saponification number of from 100 to 300 mg KOH/g.

4. The composition according to claim 1, wherein said composition comprises
   from 20 to 75 parts by weight of A),
   from 20 to 75 parts by weight of B), and
   from 0.01 to 50 parts by weight of water.

5. The composition according to claim 1, wherein B) comprises at least 70% by weight of the glycerol esters in the composition.

6. The composition according to claim 1, wherein the carboxylic acids of the carboxylic esters of components A) and B) are selected from fatty acids.

7. The composition according to claim 1, wherein the carboxylic acid of the sorbitan carboxylic ester of A) is selected from caprylic acid and capric acid.

8. The composition according to claim 1, wherein the carboxylic acid of the glycerol carboxylic ester of B) is selected from unsaturated or branched fatty acids.

9. A process for preparing a cosmetic or pharmaceutical formulation, in particular having a viscosity of from 500 to 15,000 mPa s, measured at 25° C. with a Brookfield viscometer using spindle 62 and at 30 rpm, comprising the process steps of
I) providing a composition according to claim 1,
II) mixing the composition with further cosmetic or pharmaceutical formulation constituents to obtain a formulation having a content of component A) and component B) in sum total in a range of from 0.1% by weight to 5.0% by weight of the cosmetic or pharmaceutical formulation.

10. The process according to claim 9, wherein in process step II) a water content is set in a range of from 50% by weight to 95% by weight of the cosmetic or pharmaceutical formulation.

11. The process according to claim 9 comprising the process step of
III) adjusting the pH to a range of from 4.0 to 8.0.

12. The composition according to claim 1, wherein
A) has at least one sorbitan carboxylic ester of at least one carboxylic acid selected from carboxylic acids having from 8 to 10, carbon atoms and wherein all sorbitan carboxylic esters present in A) together have on average a degree of esterification of from 1.3 to 1.7 carboxylic acid radicals per sorbitan carboxylic ester,
B) at least one glycerol carboxylic ester of at least one carboxylic acid selected from carboxylic acids having from 12 to 18 carbon atoms,
wherein A) and B) in sum total are present to an extent of at least 75% by weight of the composition.

13. The composition according to claim 1, wherein A) has a saponification number of from 160 to 260 mg KOH/g.

14. The composition according to claim 1, wherein B) has a saponification number of from 130 to 230 mg KOH/g.

15. The composition according to claim 1, wherein B) comprises at least 80% by weight of the glycerol esters in the composition.

16. The composition according to claim 1, wherein the carboxylic acid of the sorbitan carboxylic ester A) is a mixture of caprylic acid and capric acid.

17. The composition according to claim 1, wherein the carboxylic acid of the sorbitan carboxylic ester of A) is a mixture of caprylic acid and capric acid, with a ratio by weight of caprylic acid to capric acid in a range from 6:1 to 2:1.

18. The composition according to claim 1, wherein the carboxylic acid of the glycerol carboxylic ester of B) is oleic acid.

19. The process according to claim 9, wherein mixing the composition with further cosmetic or pharmaceutical formulation constituents to obtain a formulation having a content of component A) and component B) in sum total in a range of from 0.2% by weight to 2.5% by weight of the cosmetic or pharmaceutical formulation.

* * * * *